United States Patent [19]

Acharya

[11] Patent Number: 5,110,605

[45] Date of Patent: May 5, 1992

[54] CALCIUM POLYCARBOPHIL-ALGINATE CONTROLLED RELEASE COMPOSITION AND METHOD

[75] Inventor: Ramesh N. Acharya, Lake Forest, Ill.

[73] Assignee: Oramed, Inc., Mundelein, Ill.

[21] Appl. No.: 570,340

[22] Filed: Aug. 21, 1990

[51] Int. Cl.⁵ .................... A61K 47/32; A61K 47/36; A61K 9/10; A61K 9/16

[52] U.S. Cl. .................... 424/487; 424/484; 424/488; 424/479; 424/482; 424/422; 424/427; 424/430; 424/434; 424/435; 424/436; 424/457; 424/470; 424/479; 424/482; 424/461; 424/462; 424/443; 424/499; 424/501

[58] Field of Search ............... 424/484, 487, 488, 479, 424/482, 81

[56] References Cited

U.S. PATENT DOCUMENTS

| | | | |
|---|---|---|---|
| 3,640,741 | 2/1972 | Etes | 106/170 |
| 4,029,815 | 6/1977 | Sherlock et al. | 514/575 |
| 4,140,763 | 2/1979 | Bachrach et al. | 424/89 |
| 4,615,697 | 10/1986 | Robinson | 604/890 |
| 4,867,979 | 9/1989 | Sheth et al. | 514/867 |
| 4,900,552 | 2/1990 | Saavordeker et al. | 424/422 |
| 4,988,679 | 1/1991 | Chavkin et al. | 514/53 |

Primary Examiner—Thurman K. Page
Assistant Examiner—E. J. Webman
Attorney, Agent, or Firm—Leydig, Voit & Mayer

[57] ABSTRACT

A polymeric complex composition comprising a reaction complex formed by the interaction of a polycarbophil component with alginic acid or a salt thereof, said interaction being performed in the presence of a divalent cation and in the presence of an active agent selected from the group consisting of medicinal agents and cosmetic agents. There is also described a method of controlled release treatment comprising the steps of providing such a polymeric complex and an effective amount of an active agent selected from the group consisting of medicinal agents and cosmetic agents contained within said complex, and contacting an area of skin or mucous membrane to be treated with said composition for a sufficient period of time allow a therapeutically effective amount of said active agent to be released from the complex.

13 Claims, No Drawings

CALCIUM POLYCARBOPHIL-ALGINATE CONTROLLED RELEASE COMPOSITION AND METHOD

BACKGROUND OF THE INVENTION

This invention relates to a certain pharmaceutical dosage forms, and in particular to certain polymeric complexes which are suitable for achieving controlled or sustained delivery of an active composition. The compositions are especially useful for buccal, gingival and oral controlled release of active compositions.

BACKGROUND OF THE INVENTION

Delivery of pharmaceutical compositions through the use of polymeric carriers is a well known technique. U.S. Pat. No. 4,615,697 to Robinson provides an excellent review of this subject, especially as it relates to the use of bioadhesive compositions for buccal administration. The buccal delivery systems disclosed in Robinson utilize known bioadhesives to hold the polymeric system in place in the buccal cavity after insertion therein. The drug is released from a bioadhesive matrix and absorbed into the buccal lining. The compositions disclosed in Robinson provide a means of trans-mucosal delivery of therapeutic agents that are subject to poor bioavailability due to solubility limitations, polarity considerations, degradation due to pH, enzymatic exposure or "first pass" metabolism by the liver or gastrointestinal enzymes after oral ingestion. However, such delivery systems, although of general utility have certain disadvantages in actual application.

U.S. Pat. No. 4,900,552 provides a composition for releasing active ingredients in the buccal cavity itself for an extended period of time. The composition of that patent comprises a trilaminate film segment capable of delivering an active ingredient within the buccal cavity while attached to a wall of that cavity. The trilaminate film segment includes a hydratable bioadhesive base layer, a non-adhesive reservoir layer and a water-impermeable barrier sandwiched between and bonded to the base layer and the reservoir layer. Such a composition is by its very nature a complex structure requiring detailed formulation techniques to achieve the desired composition.

Alginic acid, including its salts, has also been used in various forms and combinations for purposes of providing bioadhesive compositions for the administration of active compositions. As one example thereof, the use of cross-linked alginate gum gel is described in U.S. Pat. No. 3,640,741 to Etes as being suitable for use as the bioadhesive.

SUMMARY OF THE INVENTION

The present invention provides a polymeric complex which is formed through the interaction of a polycarbophil type composition, or a salt thereof, with alginic acid, or a salt thereof, in the presence of a divalent cation. The resulting product is especially useful as a carrier for active compositions, such as pharmaceuticals and the like, and provides a means for achieving a rate-controlled release of the active composition.

Because of the nature of the polymeric complexes of the present invention, the compositions of the present invention also exhibit some bioadhesive properties. The polymeric complexes also may be made to contain an active composition, such as a pharmaceutical, by incorporating such an agent into either the polycarbophil component or the alginic acid component, prior to forming the complex between the two constituents.

The present invention provides several advantages and benefits, including an improved composition and method for the controlled release of an active composition to the skin or mucosa over a period of time. The compositions are not noticeably irritating to the skin or mucosa with which they are contacted and they may contain substantially any medicinal agent or cosmetic agent.

The present invention also provides a method of controlled release treatment comprising providing a polymeric complex carrier and a therapeutically effective amount of an active composition, wherein the polymeric complex carrier is formed by the interaction of a polycarbophil component with an alginic acid component, in the presence of a divalent cation and the active composition, and contacting an area of skin or mucous membrane to be treated with said composition for a sufficient period of time to allow a therapeutically effective amount of said active composition to be released from the complex.

Other benefits and advantages of the present invention will be apparent to those skilled in the art from the Detailed Description, Examples and Claims that follow.

DETAILED DESCRIPTION OF THE INVENTION

The present invention relates to polymeric complexes which may be bioadhesive compositions, and which may be used as controlled release carriers, and to methods for the use of such complexes. The complex compositions of the present invention are formed through interaction of a polycarbophil type composition with an alginic acid component, in the presence of a divalent cation. Preferably, the divalent cation is initially present in the form of a salt with the polycarbophil type composition. The compositions also typically include an effective amount of an active composition which is incorporated in the polymeric complex. As indicated, due to the structure of the polymeric complexes of the present invention, the complexes may also be considered to be bioadhesives. Varying degrees of bioadhesive properties are exhibited by the complexes, as the alginic acid component is itself a bioadhesive. Calcium polycarbophil, which is the preferred form of the polycarbophil component, has no bioadhesive properties.

The term bioadhesive, as used herein, is a material that adheres to a mucosal tissue surface in-vivo and/or in-vitro upon hydration. Such adhesion will adherently localize the polymeric complex onto the mucus membrane.

The compositions of the present invention are designed for use on the skin and mucus membranes (mucosa) of an animal body, such as that of a human, to which the compositions adhere in the presence of a sufficient amount of water to swell the compositions. The compositions, when containing an active composition, are adhered to mucosa or skin and controllably release the active composition to the contacted body area for a period of time, and cause the active composition to be sorbed (absorbed or adsorbed) at least at the vicinity of the contacted body area.

The compositions of this invention are substantially non-toxic to the animals in which or on which they are placed, aside from any toxicity associated with the active composition alone. Thus, when contacted with and adhered to skin or mucosa, the compositions cause no apparent whitening or blistering effects due to the compositions. In addition, adverse immunologic effects from the use of compositions of this invention in animals should not be present.

The phrases "pharmaceutically acceptable", "cosmetically acceptable", "physiologically tolerable" and "medicinally inert" are used herein to mean that the material so described may be used for treatments in or on humans or other mammals without causing ill effects, such as toxicity, blistering or whitening of mucosa or skin tissues, and that those materials are not themselves active compositions or bioadhesives, as those terms are used herein.

ACTIVE COMPOSITIONS

The active compositions useful herein are selected generally from the classes of medicinal agents and cosmetic agents. Substantially any agent of these two classes of materials may be used in the present invention including both solid and liquid active compositions.

Thus, the active composition may be a medicinal agent, an agent for treating an internal condition, an agent for treating a mental health condition, an antibiotic active composition, a chemotherapeutic agent, an anti-inflammatory agent, a high molecular weight protein or polypeptide treating agent, or the like. The active composition may also be a cosmetic agent such as a sun screen, a skin softener, an acne treating agent, a moisturizing agent and emollient, or the like. The active composition may also be a nutritional agent.

Exemplary medicinal agents include agents for treating cardiovascular conditions such as chlorothiazide (diuretic), propranolol (antihypertensive), hydralazine (peripheral vasodilator), isosorbide or nitroglycerin (coronary vasodilators), metoprolol (beta blocker), procainamide (antiarrythmic), clofibrate (cholesterol reducer) or coumadin (anticoagulant); agents for treating internal conditions such as conjugated estrogen (hormone), tolbutamide (antidiabetic), levothyroxine (thyroid conditions), propantheline (antispasmodic), cimetidine (antacid), phenyl propanolamine (antiobesity), atropine or diphenoxalate (antidiarrheal agents), docusate (laxative), or prochlorperazine (antinauseant); agents for treating mental health conditions such as haloperidol or chlorpromazine (tranquilizers), doxepin (psychostimulant), phenytoin anticonvulsant), levodopa (antiparkinism), benzodiazepine (antianxiety) or phenobarbital (sedative); anti-inflammatory agents such as fluorometholone, acetaminophen, phenacetin, aspirin, hydrocortisone, or prednisone; anti-histamines such as diphenhydramine hydrochloride or dexchlorpheniramine maleate; antibiotics such as sulfanilamide, sulfamethizole, tetracycline hydrochloride, penicillin and its derivatives, cephalosporin derivatives or erythromycin; chemotherapeutic agents such as sulfathiazole, doxorubicin, cisplatin or nitrofurazone; topical anaesthetics such as benzocaine; cardiac tonics such as digitalis or digoxin; antitussives and expectorants such as codeine phosphate, dextromethorphan or isoproterenol hydrochloride; oral antiseptics such as chlorhexidine hydrochloride or hexylresorcinol; enzymes such as lysozyme hydrochloride or dextronase; birth control agents such as estrogen; opthalmic treating agents such as timolol or gentamycin, and the like. In addition, medicinal treating agents may also include whole proteins such as the VP3 capsid protein (also known as the VP Thr and VPl capsid proteins in other nomenclature systems) of foot-and-mouth disease virus described in U.S. Pat. No. 4,140,763 as being useful as the active ingredient in a vaccine against foot-and-mouth disease, insulin or interferon; polypeptide treating agents such as endorphins, human growth hormone, or bovine growth hormone, or still lower molecular weight polypeptides or conjugates of those polypeptides linked protein carriers as are described in Sutcliffe et al., Science, 219, 660–666 (1983). Exemplary cosmetic agents include sun screens such as p-dimethylaminobenzoic acid or glyceryl p-aminobenzoate, a skin softener such as urea, keratolytic agents such as salicylic acid; acne treating agents such as benzoyl peroxide or sulfur; perfumes, and the like. Nutritional agents such as vitamins and/or minerals like riboflavin and iron, respectively, may also comprise useful active compositions herein.

The active composition may be used singly or as a mixture of two or more such agents.

Other active ingredients that can be present in the compositions of the present invention include breath fresheners and flavors, e.g., spearmint oil, peppermint oil, cinnamaldehyde, cetyl pyridinium chloride, menthol saccharin sodium, glycyrrhizin, malt syrup, citric acid, tartaric acid, lemon oil, citrus flavor, and the like, sodium fluoride and the like, anti-plaque/anti-bacterial compositions suitable to treat or prevent periodontal disease, e.g., chlorobutanol, chlorothymol, chlorhexidine, their salts, and the like, dental pain control ingredients, e.g., benzocaine, lidocaine and the like.

One or more adjuvants may also be included with an active composition. Exemplary of useful adjuvants are chelating agents such as ethylenediaminetetracetic acid (EDTA) that bind calcium ions and assist in passage of medicinal agents through the mucosa and into the blood stream. Another illustrative group of adjuvants are the quaternary nitrogen-containing compounds such as benzalkonium chloride that also assist medicinal agents in passing through the mucosa and into the blood stream.

In addition to the above ingredients, there may also be incorporated other additives selected from among the various pharmaceutically acceptable additives available to the those skilled in the art for the purpose of obtaining desirable processing and physical qualities including enhancement of the dispersibility and stability of the active ingredient. Such additives which can be used in addition to the active ingredient include the following substances: stabilizers/preservatives, e.g., parahydroxybenzoic acid alkyl esters, antioxidants, antifungal agents, and the like; coloring agents, e.g., aluminum lake, titanium dioxide, and the like; excipients/-disintegration modulating agents, e.g., magnesium silicate, silicic acid anhydride, aluminum silicate, calcium carbonate, magnesium aluminum metasilicate, calcium hydrogen phosphate, and the like; stearic acid and its salts; palmitic acid; talc; and other substances known as emulsifiers, dispersants, binders, thickeners and the like.

DOSAGE FORMS

A composition of this invention may be provided in a variety of physical forms. For example, a composition may be an intimate mixture of the polymeric complex and active composition in either dry form, as a semi-solid or as a liquid suspension. The composition may also be provided as a three-dimensional structure such as a capsule, a capsule aggregate, a film or laminate. When provided as a three-dimensional structure, the active composition is contained in a medicinally inert matrix and the structure defines at least one surface on which the polymeric complex is disposed.

The compositions of the present invention also may also be employed with suppositories for rectal or vaginal administration. In such embodiments, the polymeric complex may be coated on the surface of an active composition-containing suppository or it may be dispersed therein.

The active composition is present in the compositions of this invention in an amount that is sufficient to prevent, cure and/or treat a condition for a desired period of time for which the composition of this invention is to be administered, and such an amount is referred to herein as "an effective amount". As is well known, particularly in the medicinal arts, effective amounts of medicinal agents vary with the particular agent employed, the condition being treated and the rate at which the composition containing the medicinal agent is eliminated from the body, as well as varying with the animal in which it is used, and the body weight of that animal. Consequently, effective amounts of active compositions may not be defined for each agent. Thus, an effective amount is that amount which in a composition of this invention provides a sufficient amount of the active composition to provide the requisite activity of active composition in or on the body of the treated animal for the desired period of time, and is typically less than that amount usually used.

Inasmuch as amounts of particular active compositions in the blood stream that are suitable for treating particular conditions are generally known, as are suitable amounts of active compositions used in cosmetics, it is a relatively easy laboratory task to formulate a series of controlled release compositions of this invention containing a range of such active compositions to determine the effective amount of such an active composition for a particular composition of this invention. While the effective amount for all active compositions cannot be stated, typical compositions of this invention may contain about one microgram to about one gram of active composition per dose administered. More preferably, a composition of this invention may contain about one microgram to about 400 milligrams per dose.

The dosage form can be packaged in unit dose blister packs, pouches in a carton, vials with screw or flip-top lids, bottles with screw or flip-top lids, or any other convenient package form.

POLYCARBOPHIL COMPONENT

Several types of materials are suitable for forming the polycarbophil type composition component. The polymer contains a plurality of a repeating unit of which at least about 80 percent contain at least one carboxyl functionality and about 0.05 to about 1.5 percent cross-linking agent substantially free from polyalkenyl polyether, with the percentages being based upon the weights of the unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, this material is a reaction product of the polymerization of only a carboxyl-functional monomer and a cross-linking agent. Also in more preferred practice, this component contains about 0.1 to about 1 percent by weight of polymerized cross-linking agent. This type of polymer is disclosed in U.S. Pat. No. 4,615,697 to Robinson which is incorporated herein by reference, and certain species of this type of polymer is commercially available under the generic name "polycarbophil".

A polycarbophil type composition polymer useful herein may thus be defined as a reaction product of the copolymerization of at least 80 weight percent monoethylenically unsaturated carboxy-functional monomer and about 0.05 to about 1.5 weight percent of a cross-linking agent free of polyalkenyl polyether. The remaining monomers that may be present to constitute 100 percent by weight of the monomers are discussed below.

In addition to the above two ingredients, the polycarbophil type polymer may also include polymerized monoethylenically unsaturated repeating units such as C1-C6 alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2-3 carbon atoms such as hydroxyethyl methacrylate, hydroxypropyl acrylate and tetraethylene glycol monoacrylate; methacrylamide, acrylamide and their C1-C4 mon- and di-alkyl derivatives such as N-methyl acrylamide, N-butyl methacrylamide and N,N-dimethyl acrylamide; styrene; and the like as are known in the art as being copolymerizable with the above described carboxyl functionality-containing monomers and cross-linking agents. The polymers most preferably are prepared from only the monoethylenically unsaturated carboxy-functional monomer and the cross-linking agent.

The polycarbophil type composition useful herein may be prepared by conventional free radical polymerization techniques utilizing initiators such as benzoyl peroxide, azobisisobutyronitrile, and the like, are polymerized in an aqueous medium, and are not agglomerated by steam action. A particularly preferred polyhydrophil component that is commercially available is that material sold under the designation calcium polycarbophil by the B. F. Goodrich Co. of Cleveland, Ohio. The United States Pharmacopeia, 1990 edition, United States Pharmacopeial Convention, Inc., Rockville, Md., at page 218, indicates that calcium polycarbophil is a calcium salt of polyacrylic acid cross-linked with divinyl glycol that has a calcium content of not less than 18% and not more than 22% and absorbs not less than 35 grams of sodium bicarbonate solution per one gram of the powder in the test for Absorbing power.

THE ALGINIC ACID COMPONENT

Alginic acid is a purified polysaccharide, linear polymer which is extracted from seaweed and is available in many forms, especially as a calcium, potassium, or sodium salt, or as propylene glycol alginate. Preferably, the sodium salt is employed in the present invention.

DIVALENT CATION AND pH CONSIDERATIONS

The interaction of the polycarbophil type composition component with the alginic acid or alginate must occur in the presence of a divalent cation. Preferably, the divalent cation is calcium, although it may also be magnesium. In certain instances divalent iron, copper, or chromium may also be used. The divalent cation should be present in an amount from about 5 to about 25 percent and preferably from about 18 to about 22 percent, based on the weight of polycarbophil. Most preferably, the calcium cation is originally present as the salt of the polycarbophil type composition. However, it may also be initially present as the salt of the alginic acid or may otherwise introduced as a calcium ion-containing compound, such as calcium chloride, calcium gluconate, calcium hydroxide, or the like.

The interaction of the polycarbophil type composition with the alginic acid or alginate should be at a pH of from about 3 to about 10, preferably at a pH from about 6.5 to about 7.5. Interaction at such a pH will assure that the polycarbophil type composition and alginic acid components form the desired complex. It is believed that the complex is formed through a bridging of carboxyl groups of the two polymeric components that occurs through the divalent cation.

INTERACTING THE POLYCARBOPHIL COMPONENT AND ALGINIC ACID

The polycarbophil type component may be interacted with the alginic acid in any suitable means. Preferably, the alginic acid is present in the form of its sodium salt, while the polycarbophil type composition is present in the form of its calcium salt. Most preferably, the polycarbophil type composition component is that sold under the designation calcium polycarbophil. The commercially available calcium polycarbophil is not itself a bioadhesive.

Prior to interacting the two components, an active composition as described previously may be incorporated into one or both of the polycarbophil type composition and the alginate. The incorporation may be through dissolution, or dispersion of the active composition in a matrix of the alginate, for example, as a solid or a semi-solid or the alginate may be in an aqueous or mixed solvent system.

The alginate component may be employed in an amount from about 0.1 to about 99.9 percent, based upon the total weight of the composition. The amount of polycarbophil type composition will affect the consistency of the final product. Accordingly, the final product may vary from a water-like consistency to that of a solid dry powder. Likewise, the amount of calcium polycarbophil type composition may vary from about 0.1 to about 90.0 percent, based upon the total weight of the composition. The polycarbophil type composition may be introduced into the reaction as a solid or in an aqueous or a mixed solvent system. All percentages expressed in this application are by weight unless stated otherwise.

The interaction of the two components in the presence of water or other polar solvent and in the presence of a bivalent cation, especially calcium, results in the formation of a complex which may be described as membrane type matrix, specifically at the interface of the two polymers. The resulting matrix structure then acts to control the diffusion or other transport of the active composition within and from the matrix itself.

The desired level of controlled or sustained release will vary, depending upon the ratio of the components employed, the particular active composition, the method of incorporation, the order of mixing of the components, and the like. Additional additives may also be present which may modify the characteristics of the matrix and its release properties.

Preferably, the active composition is incorporated into the alginate, prior to the interaction with the polycarbophil type composition component.

GENERAL FORMULATION CONSIDERATIONS

In typical practice, the ratio by weight of the polymeric complex to the active composition in the composition is about 200,000:1 to about 1:100. In preferred practice, however, the weight ratio of polymeric complex to active composition is about 1,000:1 to about 10:1. Those weight ratios are determined using dry ingredients.

In addition to the active composition and polymeric complex, the compositions of this invention may also contain pharmaceutically or cosmetically acceptable diluents and/or one or more materials present as a medicinally inert matrix. For example, a useful polymeric complex may be coated on the surface of a pill containing the active composition and appropriate diluents to form the pill and thereby form a composition of this invention. Exemplary compositions containing a medicinally inert matrix are discussed hereinafter. In addition, one or more lubricants, plasticizing agents, binders, vehicles, coloring agents, taste and/or smell controlling agents, and the like may also be present.

A composition of this invention may contain an intimate mixture of the polymeric complex and the active composition. That intimate mixture may, for example, be a mixture of dry solids, or of the active composition dissolved or suspended in a pharmaceutically or cosmetically acceptable (physiologically tolerable) carrier that also includes suspended particles of polymeric complex. The phrase "intimate mixture" is used herein to mean that the components of the composition are mixed substantially uniformly so that none of those components is localized. A minor amount of agitation immediately prior to use may be required for some liquid compositions of this invention to achieve an intimately mixed state when used.

Illustrative of an intimate mixture of dry composition components is an admixed powder formed from comminuted polymeric complex particles having a size sufficient to pass through a 20 mesh sieve screen and be retained on a 200 mesh sieve screen (U.S. Standard Sieve Series) admixed with similarly or smaller sized particles of an active composition such as chlorothiazide. (Hereinafter, when particles are sized to pass through one screen and be retained on a second screen, as above, the size of the passing screen mesh will be written first, followed by a virgule, "/", and then the size of the retaining screen mesh. Thus, the above passing and retaining screen mesh sizes are written "20/200".) The mixture may be provided for treatment in tablet form or within a gelatin capsule and ingested for treatment.

The size of the polymeric complex particles has some effect upon the compositions of this invention. It is apparent that the polymeric complex particles should not be so large that the composition cannot be administered without undue difficulty. For example, if the composition is to be swallowed, the polymeric complex particles must be sized to permit passage of the composition to the stomach without impeding passage of subsequently ingested foods or liquids thereto. Similarly, when the composition is to be used in the eye, finely comminuted polymeric complex particles, e.g. sized to pass through a 100 mesh sieve screen (U.S. Standard Sieve Series). are utilized so that visual impairment of the treated animal is minimized.

Typically. at the maximum. a useful polymeric complex is sized to pass through a sieve screen having a 10 mesh (U.S. Standard Sieve Series); i.e., a 2000 micron opening. Preferably, the polymeric complex particles are sized to pass through a 30 mesh sieve screen (U.S. Standard Sieve Series). Particles having a relatively small size swell more rapidly than do particles having a relatively large size, and thus, a relatively small size is preferred for the particles.

In another embodiment, the polymeric complex is swollen in an aqueous medium containing tee active composition, and the active composition is sorbed (absorbed or adsorbed) into or onto the swollen polymeric complex particles. After drying, the composition so prepared is provided for treatment as described above. The word "dry" is used herein in relation to a polymeric complex to mean that the polymeric complex does not adhere when touched with a finger within a rubber glove, and is substantially unswollen.

The controlled release composition adheres to the skin or to mucus membranes (mucosa) in the presence of sufficient water to swell the polymeric complex.

METHOD OF TREATMENT

A controlled release method of treatment is also contemplated. According to this method. a controlled release composition of this invention is provided. An area of skin or of mucus membrane to be treated is contacted with that composition. with the contacting being carried out in the presence of sufficient water to swell the polymeric complex. The composition adheres to the area contacted, releasing the active composition at a controlled rate, and causing the active composition to be sorbed at least at the vicinity of the contacted area.

Upon contact with mucus which is excreted by the lining of the buccal cavity, the polymeric complex hydrates thus adhering the buccal dosage form to the lining.

A method of controlled release treatment also constitutes an aspect of this invention. In accordance with this method, a controlled release composition containing an effective amount of active composition per dose is provided, as described before. An area of skin or mucus membrane to be treated is contacted with the provided composition. The contact is carried out in the presence of sufficient water to swell the polymeric complex and cause the polymeric complex-containing composition to adhere to the area contacted, as well as cause the controlled release of the active composition in the vicinity of that contact.

The compositions of this invention may provide the intimate contact between the active composition and the mucosa that is preferred for high molecular weight active compositions such as proteins and hormones. These compositions, through their bioadhesion, maintain the intimate contact for extended periods of time to thereby increase the relative concentration of the active composition in the vicinity of that contact.

Each of the beforedescribed compositions may be administered in accordance with this method.

The compositions of this invention may be administered by several means to provide the desired contact between the skin or mucus membrane and the composition. For example, where the active composition is a sun screen, the composition may be applied to the skin by rubbing the composition over the skin area to be treated. Where the conjunctival mucosa are to be contacted. the aqueous composition described above may be instilled into the precorneal pockets of the eyes. Where the buccal. nasal. anal and/or vaginal mucosa are to be contacted. the composition may be applied by hand, forceps or other suitable instrument. Where the mucosa of the stomach and/or intestines are to be contacted, the composition is typically swallowed. or implanted surgically, and contact with the mucus membrane is achieved by the contraction of the stomach or intestines and/or by the carrying action provided by passage of gastric fluids therethrough.

The composition is left in place (contact maintained) for a time sufficient for the active composition to be released over a controlled period. and thereby provide its medicinal or cosmetic function to the treated animal. In most circumstances. some unused. still active. controlled release composition and the remainder of the composition administered are eliminated from the body by a natural bodily mechanism, such as by dispersion or erosion caused by an aqueous body fluid such as saliva, tears, gastric fluid or vaginal secretions. In other instances, such as where the active composition is contained in a medicinally inert matrix such as a ethylene-vinyl acetate copolymer or cross-linked elastomer that is ingested, the flushing action provided by the flow of gastric fluids and stomach contractions ultimately results in excretion in the feces of any unused composition and of the remainder of the administered composition.

EXAMPLE 1

This example demonstrates the manufacture of a composition of the present invention in which benzocaine is incorporated for the purposes of achieving controlled release. Five-hundred milligrams of sodium alginate (Algin HV from Kelco) are mixed with eighty milligrams of benzocaine, USP. The resultant mass is granulated using 10% glycerol solution in purified water, USP, as the binding solution. Propylene glycol solution may also be employed in place of the glycerol. The resultant granulated mass is further mixed with five-hundred milligrams of calcium polycarbophil, USP. The mass is further granulated with the aid of purified water as a binder. Corn starch could also be employed at this granulation stage. An additional twenty milligrams of benzocaine are added to the mass with mixing. The resulting product is then conventionally formed into thin discs or wafers suitable for local administration.

The resulting discs are formulated of varying sizes, making them suitable for buccal, gingival or oral administration. The ratio of the polymeric complex material of the present invention to the weight of the active composition is approximately 10:1).

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

What is claimed is:

1. A polymeric complex composition comprising a reaction complex formed by the interaction of (1) about 0.1% to about 90% calcium polycarbophil component which is a water-swellable, but water-insoluble, fibrous, cross-linked carboxy-functional polymer, said polymer containing (a) a plurality of repeating units of which at least about 80 percent contain at least one carboxyl functionality, and (b) about 0.05 to about 1.5 percent cross-linking agent substantially free from polyalkenyl polyether, said percentages being based upon the weights of unpolymerized repeating unit and cross-linking agent, respectively with (2) from about 0.1 to about 99, percent of alginic acid or a salt thereof, said interaction being performed in the presence of an active agent selected from the group consisting of medicinal agents and cosmetic agents, said interaction being at a pH from about 3 to about 10, the calcium polycarbophil being originally present, prior to said interaction, in the form of the calcium salt, having a calcium, and wherein the ratio of said reaction complex to said active agent is about 200,000:1 to about 1:100'.

2. The composition according to claim 1 wherein said polymeric complex composition is in the form of comminuted particles capable of passing through the screen of a sieve having a 100 mesh size, U.S. Standard Sieve Series, and said active agent is present as a saturated solute in a physiologically acceptable aqueous carrier.

3. The composition according to claim 1 wherein said active agent is contained in a medicinally inert matrix in the form of a three-dimensional structure having at least one surface portion, and said polymeric complex composition is disposed on at least said one surface portion.

4. The composition according to claim 1 wherein said active agent constitutes an agent for treating cardiovascular conditions.

5. The composition according to claim 1 wherein said active agent constitutes an agent for treating internal diseases and disorders.

6. The composition according to claim 1 wherein said active agent constitutes an anti-inflammatory agent.

7. The composition according to claim 1 wherein said active agent constitutes an anti-bacterial agent.

8. The composition according to claim 1 wherein at least about 90 percent of said polymer repeating units contain at least one carboxyl functionality.

9. The composition according to claim 1 wherein at least about 95 percent of said polymer repeating units contain at least one carboxyl functionality.

10. The composition according to claim 1 wherein said polymer contains about 0.1 to about 1 percent by weight of polymerized cross-linking agent.

11. The composition according to claim 1 wherein said carboxyl functionality is provided by polymerized acrylic acid.

12. A method of controlled release treatment comprising the steps of:
  (a) providing a polymeric complex and an active agent selected from the group consisting of medicinal agents and cosmetic agents contained within said complex, said polymeric complex comprising a reaction complex formed by the reaction of (1) 0.1% to about 90% calcium polycarbophil which is a water-swellable, but water-insoluble, fibrous, cross-linked carboxy-functional polymer, said polymer containing (a) a plurality of repeating units of which at least about 80 percent contain at least one carboxyl functionality, and (b) about 0.05 to about 1.5 percent cross linking agent substantially free from polyalkenyl polyether, said percentages being based upon the weights of the unpolymerized repeating unit and cross-linking agent, respectively, or a salt thereof, with (2) from about 0.1 to about 99.9 percent of alginic acid or a salt thereof, said interaction being performed in the presence of said active agent, said interaction being at a pH from about 3 to about 10, and the calcium polycarbophil being originally present, prior to said interaction, in the form of the calcium salt, having a calcium content of from about 5 to about 25 percent, based on the weight of the polycarbophil, and wherein the ratio of said reaction complex to said active agent is about 200,000:1 to 1:100'; and
  (b) contacting an area of skin or mucous membrane to be treated with said composition for a period of time to allow a therapeutically effective amount of said active agent to be released from the complex.

13. The method according to claim 12 wherein said composition comprises an intimate mixture of said reaction complex and said active agent.

* * * * *